(12) United States Patent
Brumfield (10) Patent No.: US 10,546,597 B2
(45) Date of Patent: Jan. 28, 2020

(54) EMOTIONAL STATE-BASED CONTROL OF A DEVICE

(71) Applicant: International Business Machines Corporation, Armonk, NY (US)

(72) Inventor: Sara C. Brumfield, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/224,765

(22) Filed: Aug. 1, 2016

(65) Prior Publication Data

US 2018/0033452 A1 Feb. 1, 2018

(51) Int. Cl.
| G10L 21/00 | (2013.01) |
| G10L 25/63 | (2013.01) |
| G10L 25/87 | (2013.01) |
| G10L 25/00 | (2013.01) |

(52) U.S. Cl.
CPC .............. G10L 25/63 (2013.01); G10L 25/87 (2013.01)

(58) Field of Classification Search
CPC ................................ G10L 25/63; G10L 25/87
USPC ................... 704/231, 240, 251, 270
See application file for complete search history.

(56) References Cited

U.S. PATENT DOCUMENTS

| 5,956,675 A * | 9/1999 | Setlur ..................... G10L 15/22 |
| | | 704/231 |
| 6,230,121 B1 * | 5/2001 | Weber ................... A61B 5/1112 |
| | | 704/202 |
| 9,521,973 B1 * | 12/2016 | Beiski ..................... A61B 5/168 |
| 9,548,046 B1 * | 1/2017 | Boggiano ............... G10L 15/05 |
| 2008/0195980 A1 * | 8/2008 | Morris .................... G06F 3/011 |
| | | 715/864 |
| 2010/0198620 A1 * | 8/2010 | Mullenger ........... G06Q 10/087 |
| | | 705/3 |
| 2012/0230483 A1 * | 9/2012 | Bouzid ............... H04M 3/5158 |
| | | 379/201.02 |
| 2015/0290454 A1 * | 10/2015 | Tyler ..................... A61N 1/0548 |
| | | 607/134 |
| 2015/0310852 A1 * | 10/2015 | Spizzo .................... G10L 25/48 |
| | | 704/251 |

(Continued)

OTHER PUBLICATIONS

P. Mell et al., "The NIST Definition of Cloud Computing", National Institute of Standards and Technology, Information Technology Laboratory, Sep. 2011, pp. 1-7.

(Continued)

Primary Examiner — Thierry L Pham
(74) Attorney, Agent, or Firm — Law Office of Jim Boice (57) ABSTRACT

A method, system, and/or computer program product improves an emotional state for a user by activating an improvement device. A speech counter determines a current spoken word count of words spoken by a user during a current predefined time period, where the words spoken by the user are detected by a microphone. One or more processors determine a threshold spoken word count for the user, where the threshold spoken word count historically has improved an emotional state for the user. In response to the current spoken word count being less than the threshold spoken word count, one or more processors activate an improvement device, where the improvement device guides the user to increase the current spoken word count in order to improve the emotional state for the user by reaching the threshold spoken word count.

12 Claims, 5 Drawing Sheets

(56) References Cited

U.S. PATENT DOCUMENTS

2015/0318002 A1 11/2015 Karam et al.
2016/0005320 A1 1/2016 Decharms et al.
2016/0022193 A1 1/2016 Rau et al.

OTHER PUBLICATIONS

J. Chu, "Software Listen for Hints of Depression", MIT Technology Review, Nov. 4, 2009, pp. 1-6.
G. M. Gonzalez, "Computerized Speech Recognition in Psychological Assessment: A Macintosh Prototype for Screening Depressive Symptoms", Psychonomic Society, Inc., Behavior Research Methods, Instruments, & Computers, 1993, 25 (2), pp. 301-303.
C. Zlotnick et al., "The Relationship Between Quality of Interpersonal Relationships and Major Depressive Disorder: Findings From the National Comorbidity Survey", Journal of Affective Disorders, International Society for Affective Disorders, Sep. 2000, 59 (3), pp. 205-215. (Abstract Only).
L. Everett-Haynes, "Depression, Poor Social Skills Are Linked", University Communications, The University of Arizona, Jul. 8, 2010, pp. 1-3.
Anonymous, "Code Archive: Voiceid", Google, Inc., code.google.com, Retrieved Mar. 15, 2016, pp. 1-2.
E. Lisitsa, "The Positive Perspective: Dr. Gottman's Magic Ratio!" The Gottman Institute, www.gottman.com, Dec. 5, 2012, pp. 1-6.

\* cited by examiner

EMOTIONAL STATE-BASED CONTROL OF A DEVICE

BACKGROUND

The present disclosure relates to the field of hardware devices, and particularly to hardware devices that control other devices. Still more particularly, the present disclosure relates to hardware devices that control devices based on an emotional state of a user.

SUMMARY

A method, system, and/or computer program product improves an emotional state for a user by activating an improvement device. A speech counter determines a current spoken word count of words spoken by a user during a current predefined time period, where the words spoken by the user are detected by a microphone. One or more processors determine a threshold spoken word count for the user, where the threshold spoken word count historically has improved an emotional state for the user. In response to the current spoken word count being less than the threshold spoken word count, one or more processors activate an improvement device, where the improvement device guides the user to increase the current spoken word count in order to improve the emotional state for the user by reaching the threshold spoken word count.

BRIEF DESCRIPTION OF THE DRAWINGS

The novel features believed characteristic of the invention are set forth in the appended claims. The invention itself, however, as well as a preferred mode of use, further purposes and advantages thereof, will best be understood by reference to the following detailed description of an illustrative embodiment when read in conjunction with the accompanying drawings, where:

DETAILED DESCRIPTION

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

People who struggle with depression often know there are certain behaviors that keep them mentally healthy and reduce the risk of a full blown depressive period. Those behaviors and activities are relatively easy to do when they are feeling "good", but challenging to do when they are feeling "bad". The challenge is to pre-emptively engage a device that will prevent the person from feeling "bad" based on a decline in their emotional state.

Clinical research shows that being taciturn (not speaking much) and otherwise failing to interact with other people is not only a sign of depression, but may also trigger a depressive episode. Thus, the present invention monitors a spoken word count for a user. If the spoken word count is below a predefined quantity, then the present invention activates an improvement device that requires the user to speak and/or provides other depression-ameliorative environments.

For example, assume that a speech monitor worn by a user knows that a user should say 15,000 words aloud each day in order to remain in a non-depressed state. In one or more embodiments, the speech monitor may know that not only should the user speak a total of 15,000 words in a day, but should speak a certain number of words during each part of the day. For example, the speech monitor may know (based on previous correlations between the user's speech pattern and levels of depression) that a particular user is best able to avoid a depression episode if he/she ways at least 4,000 words between 7:00 AM and 10:00 AM, but needs only to say at least 2,000 words between 10:00 AM and 5:00 PM, and then needs to say at least 9,000 words between 5:00 PM and 10:00 PM in order to avoid going into a depressive state/episode.

In one or more embodiments of the present invention, the quantity of words that the user should say may be modified by other factors, such as the day of the week, season of the year, biometric sensor readings, recency of past depressive episodes, etc. Based on such factors and a current word count for the user, the system creates a graph that identifies an inadequate amount of spoken words 1) for a particular user, 2) at a particular time, 3) based on a user's biometrics, and 4) based on the user's history.

If the graph indicates that the user is in need of an intervention, then an improvement device is activated, in order to prevent the user from sliding into a depressive state.

While the present invention addresses depressive states, the system described herein may also be utilized with users having other emotional issues, such as anxiety disorders, dissociative disorders, neurocognitive disorders, and/or any other disorder for which certain quantities of spoken words are useful in ameliorating the user's symptoms.

Figure 1:
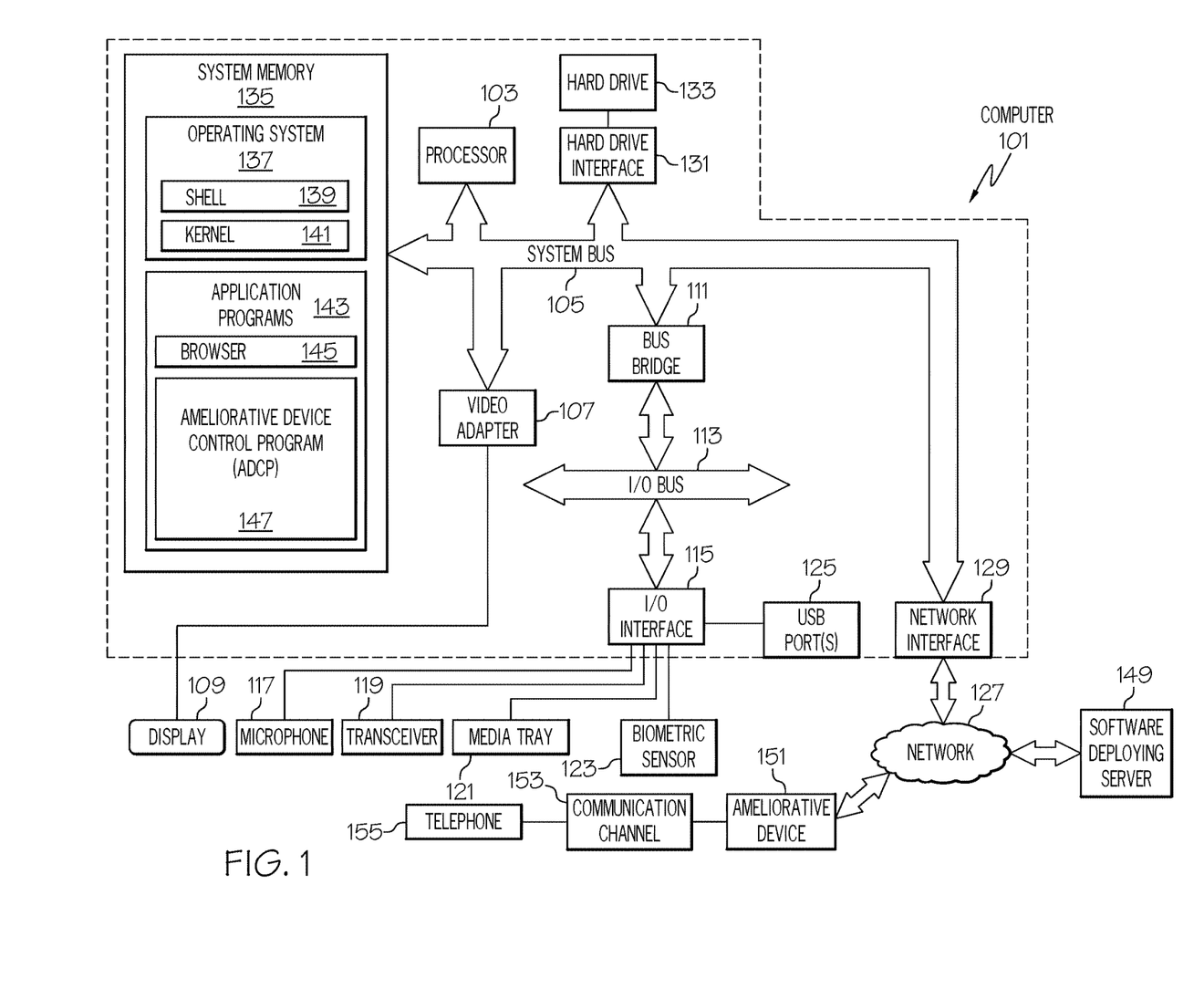
FIG. 1 depicts an exemplary system and network in which the present disclosure may be implemented.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 and/or improvement device 151 shown in FIG. 1, and/or the speech monitor 201 shown in FIG. 2.

Exemplary computer 101 includes a processor 103 that is coupled to a system bus 105. Processor 103 may utilize one or more processors, each of which has one or more processor cores. A video adapter 107, which drives/supports a display 109 (which may be a touch-screen display capable of detecting touch inputs onto the display 109), is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a microphone 117 (capable of detecting spoken words by a user), a transceiver 119 (capable of directly transmitting and receiving wireless signals to transceivers in other devices, such as an improvement device 151), a media tray 121 (which may include storage devices such as CD-ROM drives, multimedia interfaces, etc.), and external USB port(s) 125. While the format of the ports connected to I/O interface 115 may be any known to those skilled in the art of computer architecture, in one embodiment some or all of these ports are universal serial bus (USB) ports.

In an embodiment, also coupled to the I/O interface 115 is a biometric sensor 123. Various embodiments of biometric sensor 123 detect various biometric states of a user to whom the biometric sensor 123 is attached and/or directed. For example, biometric sensor 123 may be a heart monitor that measures the heart rhythm (e.g., generates an electrocardiogram, detects beats per minute, etc.) of the user. Biometric sensor 123 may be a blood pressure cuff. Biometric sensor 123 may be a galvanometer/ohmmeter that measures changes in skin resistance caused by a user sweating. Biometric sensor 123 may be a thermometer that measures a body and/or skin temperature of a user. Biometric sensor 123 may detect a respiratory rate (e.g., breaths taken per minute) of the user. Such biometric sensor readings are then used by computer 101 to determine the current physiological and/or emotional state of the user. That is, an increase in heart rate, blood pressure, skin temperature, etc., may indicate that the user is anxious.

As depicted, computer 101 is able to communicate with a software deploying server 149 and/or other devices/systems (e.g., improvement device 151) using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include an Improvement device Control Program (ADCP) 147. ADCP 147 includes code for implementing the processes described below, including those described in FIGS. 2-3. In one embodiment, computer 101 is able to download ADCP 147 from software deploying server 149, including in an on-demand basis, wherein the code in ADCP 147 is not downloaded until needed for execution. In one embodiment of the present invention, software deploying server 149 performs all of the functions associated with the present invention (including execution of ADCP 147), thus freeing computer 101 from having to use its own internal computing resources to execute ADCP 147.

Improvement device 151 is a hardware device that improves a user's emotional state, which has been identified by detecting that a particular user has spoken fewer than a predetermined number of words during a predefined period of time.

For example, in one or more embodiments of the present invention improvement device 151 is a telephone. Activation of the improvement device 151 causes a communication channel 153 to open up, thus affording (and in one or more embodiments forcing) a communication session with another telephone 155. In an embodiment, the user is guided to engage in a verbal conversation by initiating a phone call session between the two telephones.

In one or more embodiments of the present invention improvement device 151 is a recording device. When activated, the recording device prompts a user to start speaking into a microphone on the recording device, thus increasing the number of words spoken by the user.

In one or more embodiments of the present invention improvement device 151 includes features known to improve certain emotional states. For example, assume that strenuous exercise is known to reduce depression for a particular user, and the user has not said more than a predetermined number of words within a predefined period of time (e.g., the user has spoken less than 5,000 words in a day). Assume further that improvement device 151 is an exercise machine (e.g., a treadmill or a stationary bicycle) that can be adjusted to force the user to work harder when using the exercise machine (e.g., by increasing a speed or incline/slope of the tread, increasing the resistance in the pedal of the stationary bicycle, etc.). Thus, if the user has been deemed to be on a "downward slide" towards a compromised emotional state (e.g., depression) based on the user's being taciturn (saying little), then the exercise machine is adjusted to cause the user to exert more energy, thereby stopping this "downward slide".

In another embodiment, the improvement device 151 is a protective device. For example, the improvement device 151 may be a lock on a medicine cabinet, a firearm cabinet, etc., which contain items that one in a depressive state should not have access to. Thus, if the user has been deemed to be on a "downward slide" towards a compromised emotional state (e.g., depression) based on the user's being taciturn, then the cabinet will be locked, in order to protect the user from potential self-inflicted injury.

In another embodiment, the improvement device 151 is a therapeutic device. For example, the improvement device 151 may be a bright light (known to counteract seasonal adjusted depression—SAD), a video monitor connected to a video file of a picture or movie known to reduce a particular person's bouts of depression, a musical device programmed to play music known to reduce the particular person's bouts of depression, etc. Similarly, the improvement device 151 may be a stove/oven (including a microwave oven) preloaded with prepared food that is known to reduce depression when eaten by this particular user (e.g., "comfort food"). Thus, if the user has been deemed to be on a "downward slide" towards a compromised emotional state (e.g., depression) based on the user's being taciturn, then one or more of such devices will be turned on, thereby stopping this "downward slide".

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

Figure 2:
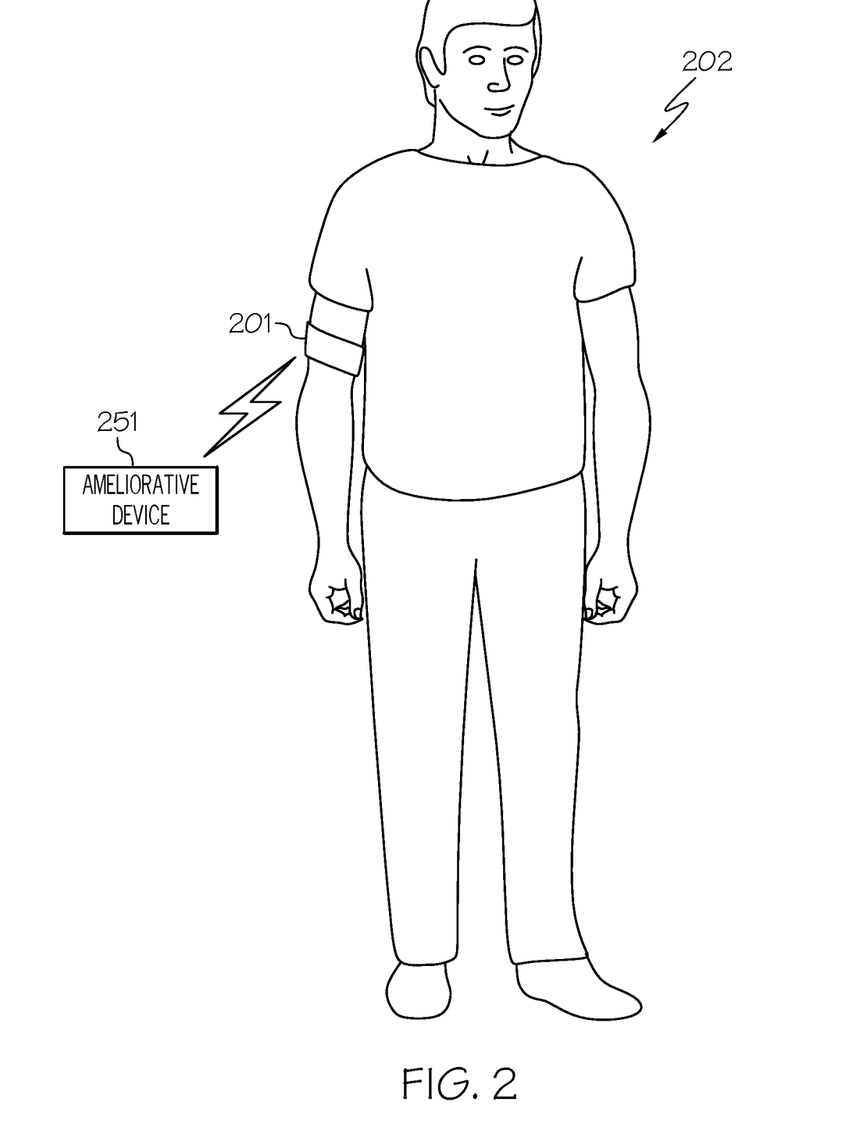
FIG. 2 illustrates a user wearing a speech monitor that detects how many words a user has spoken during a predetermined period of time.

With referenced now to FIG. 2, assume that a user 202 is wearing a speech monitor 201 (having an architecture similar in all or part to the computer 101 shown in FIG. 1), which includes a speech counter (for counting how many words the user 202 has spoken aloud during some predefined period of time) and one or more processors for determining whether this quantity of words is sufficient to halt a potential slide into a state of an emotional state (e.g., depression). That is, a microphone within the speech monitor 201 will pick up the spoken words of the user 202; the processors (e.g., processor 103 shown in FIG. 1) will retrieve a record of how many spoken words per time period (e.g., 1,000 words per hour) have been shown to prevent this particular user 202 from sliding into a depressive state; the processors will compare how many words the user 202 is currently saying compared to the record of how many spoken words per time period prevent user 202 from sliding into the depressive state; and in response to the user 202 not saying enough words, a transceiver (e.g., transceiver 119 shown in FIG. 1) will activate the improvement device 251 (analogous to the improvement device 151 shown in FIG. 1).

Figure 3:
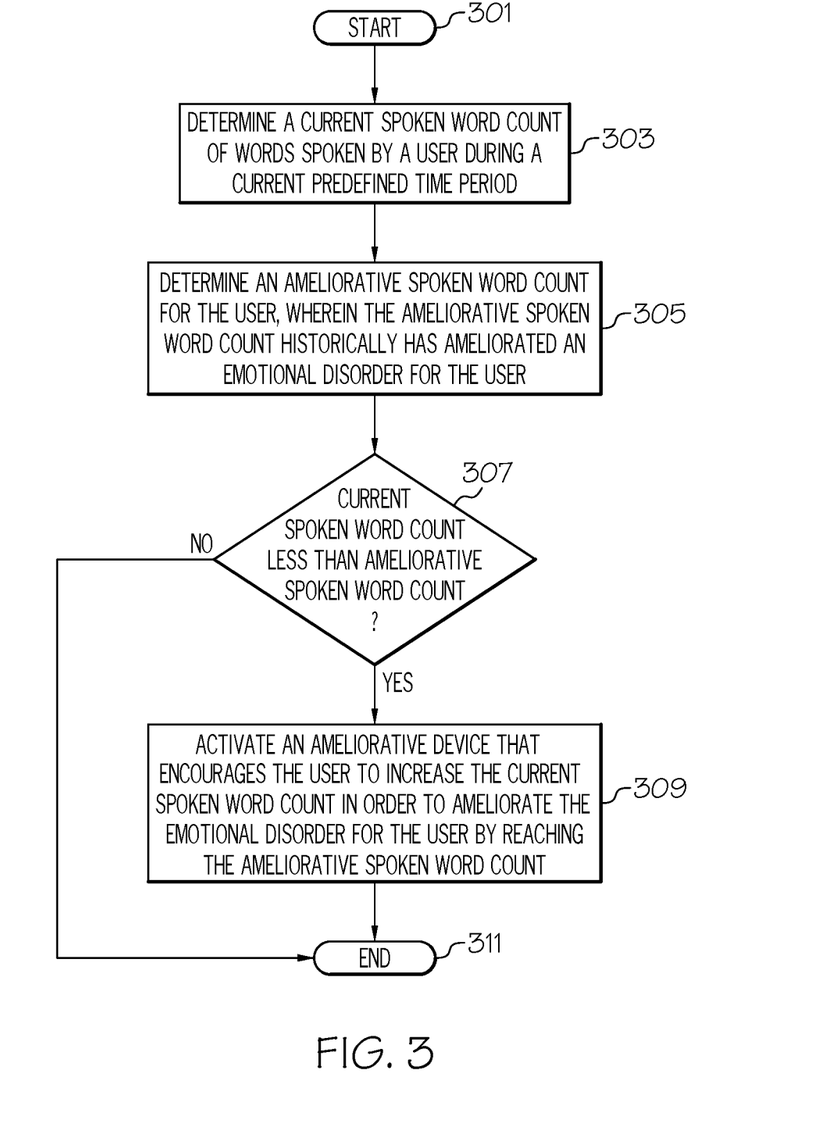
FIG. 3 is a high level flow chart of one or more steps performed by one or more processors and/or other hardware devices to control an improvement device that improves an adverse emotional state of a user.

With reference now to FIG. 3, a high level flow chart of one or more steps performed by one or more processors and/or other hardware devices to control an improvement device that reduces an adverse emotional state (emotional state) of a user is presented.

After initiator block 301, a speech counter (e.g., part of speech monitor 201 shown in FIG. 2) determines a current spoken word count of words spoken by a user during a current predefined time period, as described in block 303. As described herein, the words spoken by the user are detected by a microphone (e.g., microphone 117 shown in FIG. 1 when incorporated into the speech monitor 201).

As described in block 305, one or more processors (e.g., within computer 101 in FIG. 1 and/or speech monitor 201 shown in FIG. 2) determine a threshold spoken word count for the user. This threshold spoken word count is a quantity of spoken words by that user that has been historically shown to reduce an emotional state (e.g., depression) for the user. That is, historical data shows that if this user has spoken more than a certain number of words during a certain time period (e.g., more than 15,000 words per day), then that user is less likely to slide into a depressive state (at least for that day).

As described in query block 307, the one or more processors then compare how many words per unit of time are currently being spoken to how many words per unit of time need to be spoken by the user in order to avoid sliding into depression.

As described in block 309, in response to the current spoken word count being less than the threshold spoken word count, one or more processors activate an improvement device (e.g., improvement device 251 shown in FIG. 2), such that the improvement device guides the user to increase the current spoken word count in order to improve the emotional state for the user by reaching the threshold spoken word count.

The flow chart ends at terminator block 311.

As described herein, in an embodiment of the present invention the improvement device is a user's telephone (e.g., improvement device 151 shown in FIG. 1) that is used by the user. One or more processors (e.g., within computer 101 and/or speech monitor 201) open a communication channel (e.g., communication channel 153 shown in FIG. 1) between the user's telephone and another telephone (e.g., telephone 155 shown in FIG. 1) that is used by another person. In an embodiment, opening up communication channel 153 causes the user's phone to automatically ring, thus prompting the (potentially depressed) user to answer the phone and to talk to the user of telephone 155.

In an embodiment of the present invention, the improvement device is a recording device (e.g., a tape recorder). In one variation of this embodiment, one or more processors (e.g., within computer 101 and/or speech monitor 201) turn on the recording device, and then prompt the user to speak into the recording device (e.g., by activating a light or audible device on the recording device). For example, a message broadcast by a speaker on the recording device may prompt the user with certain aural cues (e.g., broadcasting the message "Tell me a story from your childhood" to the user), thereby prompting the user to provide an oral history from his/her childhood (and thus forcing the user to speak).

The number of words that the user needs to speak (in order to avoid sliding into an emotionally compromised state) may vary based on the time of day, the day of the week, the season of the year, the user's age, etc. For example, in order to avoid sliding into depression in the morning, the user may need to speak only 500 words per hour, while over 2,000 words per hour may be needed in the evening in order to have the same therapeutic effect. Similarly, a person may need to say aloud only 10,000 words per day between Monday and Friday, while that same person may need to speak over 20,000 words per day on Saturday and Sunday in order to have the same therapeutic effect. Similarly, a person may need to say aloud only 10,000 words per day during the summer months, while that same person may need to speak over 20,000 words per day during the winter months in order to have the same therapeutic effect.

In an embodiment of the present invention, the number of words that a particular user needs to speak over the course of some time period (e.g., daily) may vary based on his/her current state. That is, if the user is highly agitated, then he/she may need to say more words per day in order to avoid an emotional state than if the user is calm. Therefore, one or more processors (e.g., within computer 101 shown in FIG. 1) receive current biometric sensor data generated by a biometric sensor (e.g., biometric sensor 123 shown in FIG. 1) for the user. The processor(s) then adjust the threshold spoken word count (i.e., the target spoken work count for the user in order to avoid sliding into a compromised emotional state) based on the current biometric sensor data for the user.

The present invention may be implemented in one or more embodiments using cloud computing. Nonetheless, it is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
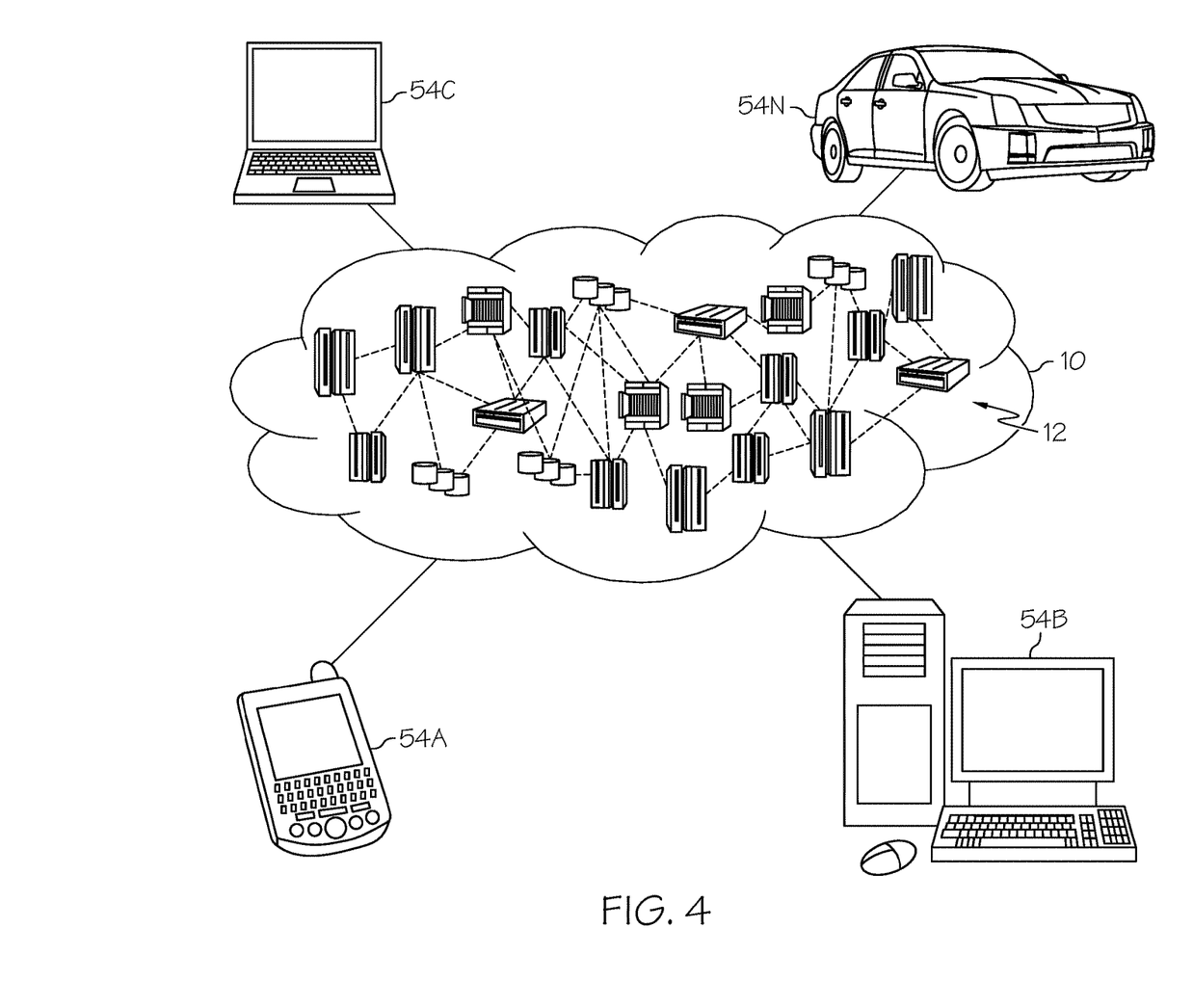
FIG. 4 depicts a cloud computing environment according to an embodiment of the present invention.

Referring now to FIG. 4, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 4 are intended to be illustrative only and that computing nodes 10 and cloud computing environment 50 can communicate with any type of computerized device over any type of network and/or network addressable connection (e.g., using a web browser).

Figure 5:
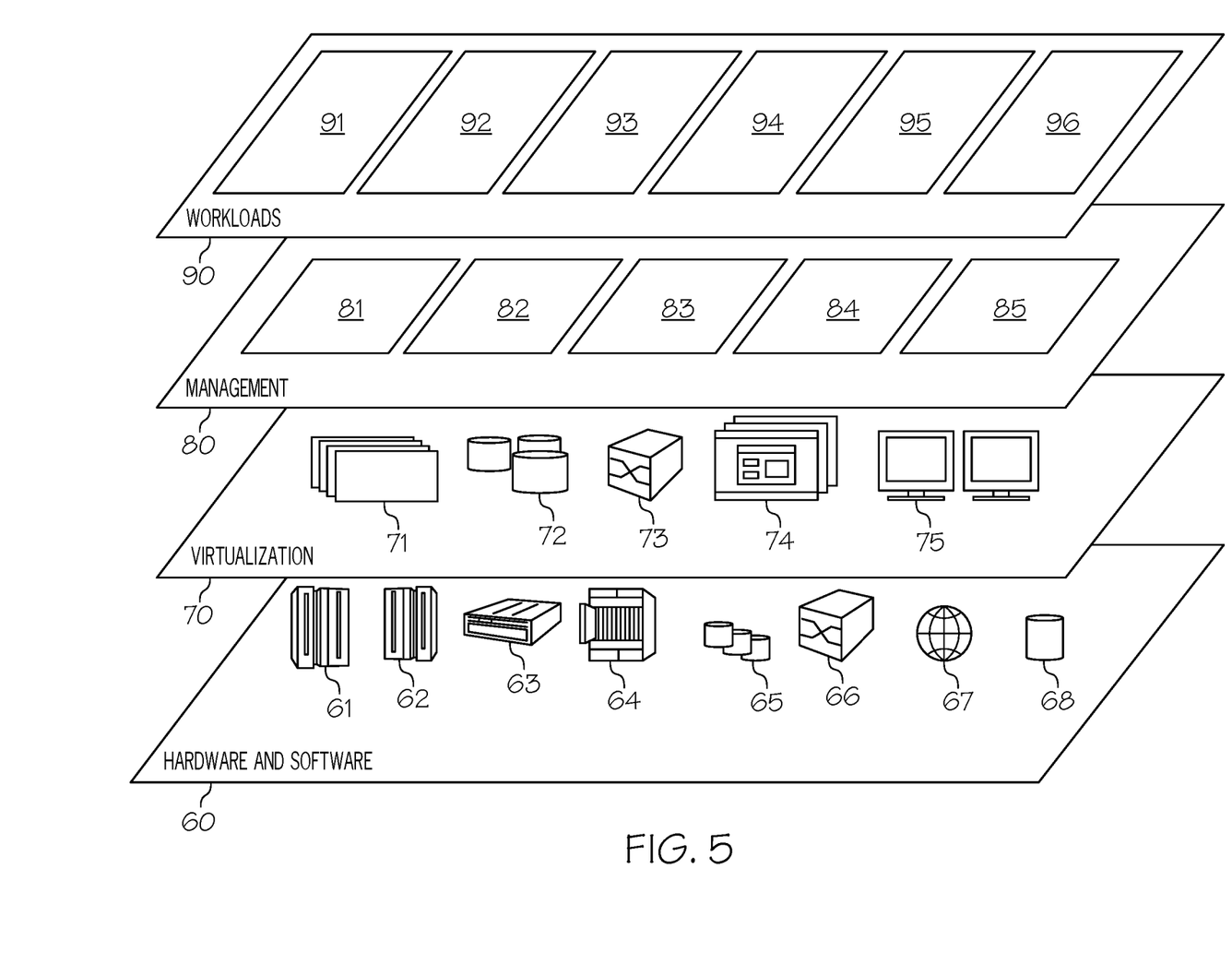
FIG. 5 depicts abstraction model layers of a cloud computing environment according to an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and spoken word count tracking processing 96, which performs one or more of the features of the present invention described herein.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
   determining, by a speech counter in a hardware speech monitor, a current spoken word count of words spoken by a user during a current predefined time period, wherein the words spoken by the user are detected by a microphone;
   determining, by the hardware speech monitor, a threshold spoken word count for the user, wherein the threshold spoken word count historically has improved an emotional state of the user;
   in response to the current spoken word count being less than the threshold spoken word count, activating, by the hardware speech monitor, an improvement device, wherein the hardware speech monitor and the improvement device are separate devices, wherein the improvement device is activated by a wireless signal automatically sent from the hardware speech monitor to the improvement device, and wherein the improvement device is a physical device that has been predetermined to improve the emotional state of the user; and
   in response to the current spoken word count being less than the threshold spoken word count, transmitting, from the hardware speech monitor to a protective lock on a container that contains a dangerous object, a signal to activate the protective lock, wherein activating the protective lock locks the container.

2. The method of claim 1, further comprising:
   adjusting, by one or more processors, the threshold spoken word count according to a current time of day.

3. The method of claim 1, further comprising:
   adjusting, by one or more processors, the threshold spoken word count according to a current day of a week.

4. The method of claim 1, further comprising:
   adjusting, by one or more processors, the threshold spoken word count according to a current season of a year.

5. The method of claim 1, further comprising:
   receiving, by one or more processors, current biometric sensor data generated by a biometric sensor for the user; and
   adjusting, by one or more processors, the threshold spoken word count based on the current biometric sensor data for the user.

6. A computer program product comprising one or more computer readable storage mediums, and program instructions stored on at least one of the one or more computer readable storage mediums, the stored program instructions comprising:
   program instructions to determine a current spoken word count of words spoken by a user during a current predefined time period, wherein the words spoken by the user are detected by a microphone;
   program instructions to determine a threshold spoken word count for the user, wherein the threshold spoken word count historically has improved an emotional state of the user;
   program instructions to, in response to the current spoken word count being less than the threshold spoken word count, activate an improvement device, wherein the hardware speech monitor and the improvement device are separate devices, wherein the improvement device is activated by a wireless signal automatically sent from the hardware speech monitor to the improvement device, and wherein the improvement device is a physical device that has been predetermined to improve the emotional state of the user; and;

program instructions to, in response to the current spoken word count being less than the threshold spoken word count, transmit, from the hardware speech monitor to a protective lock on a container that contains a dangerous object, a signal to activate the protective lock, wherein activating the protective lock locks the container.

7. The computer program product of claim 6, further comprising:
program instructions to adjust the threshold spoken word count according to a current time of day.

8. The computer program product of claim 6, further comprising:
program instructions to adjust the threshold spoken word count according to a current day of a week.

9. The computer program product of claim 6, further comprising:
program instructions to adjust the threshold spoken word count according to a current season of a year.

10. The computer program product of claim 6, further comprising:
program instructions to receive current biometric sensor data generated by a biometric sensor for the user; and
program instructions to adjust the threshold spoken word count based on the current biometric sensor data for the user.

11. A computer system comprising one or more processors, one or more computer readable memories, and one or more computer readable storage mediums, and program instructions stored on at least one of the one or more computer readable storage mediums for execution by at least one of the one or more processors via at least one of the one or more computer readable memories, the stored program instructions comprising:
program instructions to determine a current spoken word count of words spoken by a user during a current predefined time period, wherein the words spoken by the user are detected by a microphone;
program instructions to determine a threshold spoken word count for the user, wherein the threshold spoken word count historically has improved an emotional state of the user;
program instructions to, in response to the current spoken word count being less than the threshold spoken word count, activate an improvement device, wherein the hardware speech monitor and the improvement device are separate devices, wherein the improvement device is activated by a wireless signal automatically sent from the hardware speech monitor to the improvement device, and wherein the improvement device is a physical device that has been predetermined to improve the emotional state of the user; and;
program instructions to, in response to the current spoken word count being less than the threshold spoken word count, transmit, from the hardware speech monitor to a protective lock on a container that contains a dangerous object.

12. The method of claim 1, wherein the improvement device is an exercise machine used by the user, and wherein the method further comprises:
in response to the current spoken word count being less than the threshold spoken word count, adjusting, by one or more processors, an amount of resistance in the exercise machine, wherein increasing the amount of resistance in the exercise machine causes the user to exert more energy in order to further improve the emotional state of the user.

* * * * *